US010570733B2

(12) United States Patent
DiFoggio et al.

(10) Patent No.: US 10,570,733 B2
(45) Date of Patent: Feb. 25, 2020

(54) SYNTHETIC CHROMATOGRAM FROM PHYSICAL PROPERTIES (71) Applicants: Rocco DiFoggio, Houston, TX (US); Hermanus J. Nieuwoudt, Tomball, TX (US)

(72) Inventors: Rocco DiFoggio, Houston, TX (US); Hermanus J. Nieuwoudt, Tomball, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 593 days.

(21) Appl. No.: 15/369,300

(22) Filed: Dec. 5, 2016

(65) Prior Publication Data

US 2018/0156035 A1    Jun. 7, 2018

(51) Int. Cl.
*E21B 49/08* (2006.01)
*E21B 43/26* (2006.01)
*E21B 47/06* (2012.01)
*G16C 20/20* (2019.01)
*E21B 47/12* (2012.01)
*G06N 20/00* (2019.01)
*G16C 20/70* (2019.01)

(52) U.S. Cl.
CPC .............. *E21B 49/08* (2013.01); *E21B 43/26* (2013.01); *E21B 47/06* (2013.01); *E21B 47/12* (2013.01); *G16C 20/20* (2019.02); *E21B 2049/085* (2013.01); *G06N 20/00* (2019.01); *G16C 20/70* (2019.02)

(58) Field of Classification Search
CPC .......... E21B 43/26; E21B 47/06; E21B 47/12; E21B 49/08; E21B 2049/085; G06N 20/00; G16C 20/20; G16C 20/70
See application file for complete search history.

(56) References Cited

U.S. PATENT DOCUMENTS

| | | | |
|---|---|---|---|
| 5,859,430 A | 1/1999 | Mullins et al. | |
| 5,939,717 A | 8/1999 | Mullins | |
| 7,697,141 B2 | 4/2010 | Jones et al. | |
| 8,237,920 B2 | 8/2012 | Jones et al. | |
| 9,228,429 B2 | 1/2016 | DiFoggio et al. | |
| 2006/0175547 A1 | 8/2006 | DiFoggio et al. | |
| 2007/0050154 A1* | 3/2007 | Albahri | G01N 25/14 702/22 |
| 2009/0292474 A1 | 11/2009 | DiFoggio | |
| 2012/0188090 A1* | 7/2012 | Wessling | E21B 47/0002 340/853.1 |
| 2014/0309756 A1* | 10/2014 | Trygstad | G05B 13/04 700/31 |

OTHER PUBLICATIONS

International Preliminary Report on Patentability and Written Opinion of PCT/US2017/064471, dated Jun. 20, 2019, 12 pages.

* cited by examiner

*Primary Examiner* — Bryan Bui
(74) *Attorney, Agent, or Firm* — Cantor Colburn LLP (57) ABSTRACT A method for estimating a chemical composition of hydrocarbons of interest includes: performing a measurement for each physical property of a plurality of physical properties of the hydrocarbons of interest using a sensor to provide a value for each different physical property being measured; and estimating the chemical composition of the hydrocarbons of interest by using a correlation prediction function for each chemical component in the chemical composition in terms of the different physical properties being measured.

18 Claims, 10 Drawing Sheets

$D^1\ V^0\ P^0\ T^0$   First Order
$D^0\ V^1\ P^0\ T^0$
$D^0\ V^0\ P^1\ T^0$
$D^0\ V^0\ P^0\ T^1$

FIG.5A $D^2\ V^0\ P^0\ T^0$   Second Order
$D^1\ V^1\ P^0\ T^0$
$D^1\ V^0\ P^1\ T^0$
$D^1\ V^0\ P^0\ T^1$
$D^0\ V^2\ P^0\ T^0$
$D^0\ V^1\ P^1\ T^0$
$D^0\ V^1\ P^0\ T^1$
$D^0\ V^0\ P^2\ T^0$
$D^0\ V^0\ P^1\ T^1$
$D^0\ V^0\ P^0\ T^2$

FIG.5B $D^3\ V^0\ P^0\ T^0$   Third Order
$D^2\ V^1\ P^0\ T^0$
$D^2\ V^0\ P^1\ T^0$
$D^2\ V^0\ P^0\ T^1$
$D^1\ V^2\ P^0\ T^0$
$D^1\ V^1\ P^1\ T^0$
$D^1\ V^1\ P^0\ T^1$
$D^1\ V^0\ P^2\ T^0$
$D^1\ V^0\ P^1\ T^1$
$D^1\ V^0\ P^0\ T^2$
$D^0\ V^3\ P^0\ T^0$
$D^0\ V^2\ P^1\ T^0$
$D^0\ V^2\ P^0\ T^1$
$D^0\ V^1\ P^2\ T^0$
$D^0\ V^1\ P^1\ T^1$
$D^0\ V^1\ P^0\ T^2$
$D^0\ V^0\ P^3\ T^0$
$D^0\ V^0\ P^2\ T^1$
$D^0\ V^0\ P^1\ T^2$
$D^0\ V^0\ P^0\ T^3$

FIG.5C

Note that : 100% = C1wt% + C2wt% + C3wt% + C4wt% + C5wt% + C6wt% + C7pwt%

| | Methane C1wt% | Ethane C2wt% | Propane C3wt% | Butane C4wt% | Pentane C5wt% | Hexane C6wt% | Heptane+ C7pwt% | Pressure P [psi] | Temperature T [C] | Compressibility C [1/Pa] | Viscocity V [cP] | Density D [g/cc] | Sound Speed s [m/s] |
|---|---|---|---|---|---|---|---|---|---|---|---|---|---|
| Minimum | 0.0237 | 0.0105 | 0.0000 | 0.000 | 0.0000 | 0.0000 | 30.6995 | 664 | 27 | 1.934E-11 | 0.025 | 0.188 | 13 |
| Maximum | 66.2234 | 9.0150 | 7.2541 | 6.5683 | 15.7586 | 15.7586 | 99.1163 | 15092 | 146 | 1.769E-04 | 898.000 | 0.951 | 2803 |
| Mean | 6.9897 | 1.6477 | 1.9646 | 1.8612 | 2.2663 | 2.2663 | 81.7998 | 4929 | 85 | 4.209E-07 | 7.959 | 0.693 | 890 |

Regression Summary for Dependent Variable: C5wt
R= .80598259 R$^2$= .64960794 Adjusted R$^2$= .63971784
F(14,496)=65.683 p<0.0000 Std.Error of estimate: .60516

FIG.7E

Regression Summary for Dependent Variable: C6wt
R= .80552325 R$^2$= .64886770 Adjusted R$^2$= .63970160
F(13,498)=70.790 p<0.0000 Std.Error of estimate: .82635

SYNTHETIC CHROMATOGRAM FROM PHYSICAL PROPERTIES

BACKGROUND

Crude oil in different oil reserves or even in the same earth formation can have different chemical compositions. For example, different crude oils can have different chemical compositions such as different relative concentrations of methane, ethane, propane, butane, pentane, hexane, heptane and the like. Petroleum analysts and engineers would like to know the chemical compositions of oil reserves in order to efficiently recover and process the oil that they find. Gas chromatography (GC) is the standard surface laboratory method for obtaining such detailed chemical composition but retention times are very dependent upon temperature and carrier-gas flow rates and it would be extremely cumbersome to implement GC downhole, which would require a very large and costly engineering effort. Hence, it would be appreciated in the oil industry if new and efficient methods were developed to estimate a chemical composition of oil downhole in real time.

BRIEF SUMMARY

Disclosed is a method for estimating a chemical composition of hydrocarbons of interest. The method includes: performing a measurement for each physical property of a plurality of physical properties of the hydrocarbons of interest using a sensor to provide a value for each different physical property being measured; and estimating, by a processor, the chemical composition of the hydrocarbons of interest by using a correlation prediction function for each chemical component in the chemical composition in terms of the different physical properties being measured.

Also disclosed is an apparatus for estimating a chemical composition of hydrocarbons of interest. The apparatus includes: a sensor configured to perform a measurement for each physical property in a plurality of physical properties of the hydrocarbons of interest to provide a value for each different physical property being measured; and a processor configured to estimate the chemical composition of the hydrocarbons of interest by using a correlation prediction function for each chemical component in the chemical composition in terms of the different physical properties being measured.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are embodiments of methods and associated apparatuses for estimating a chemical composition of hydrocarbons such as oil in a downhole environment. While it is known that a physical property of hydrocarbons of interest can be estimated from their chemical composition, it is counter-intuitive to estimate chemical composition of hydrocarbons of interest indirectly from measurements of several physical properties of those hydrocarbons. Conceptually, this method is somewhat analogous to working backwards to determine the actual values of a set of integers by simply knowing their sum. As disclosed herein, by using measured values of several different physical properties, a process of working backwards from gross physical properties can be used to estimate corresponding detailed chemical composition of crude oils. This process can provide a synthetic chromatograph from values of physical properties of a hydrocarbon of interest.

The solution to the problem at hand is based upon measuring physical properties of a large number of samples of hydrocarbons at reservoir temperatures and pressures along with measuring their chemical compositions so as to create a training set. The weight percentages of detailed chemical composition (C1, C2, etc.) become the dependent variables in the subsequent regressions on the training set. Various composite independent variables are generated from the different types of physical properties. For simplicity of discussion, the term "physical properties" is intended to include the thermodynamic state variables—temperature and pressure. A regression of detailed chemical composition in terms of the various composite independent variables is performed to provide a statistically significant correlation and prediction function. Consequently, by measuring physical properties of hydrocarbons of interest downhole, the chemical composition of those chemical properties can be estimated using the correlation prediction function.

Figure 1:
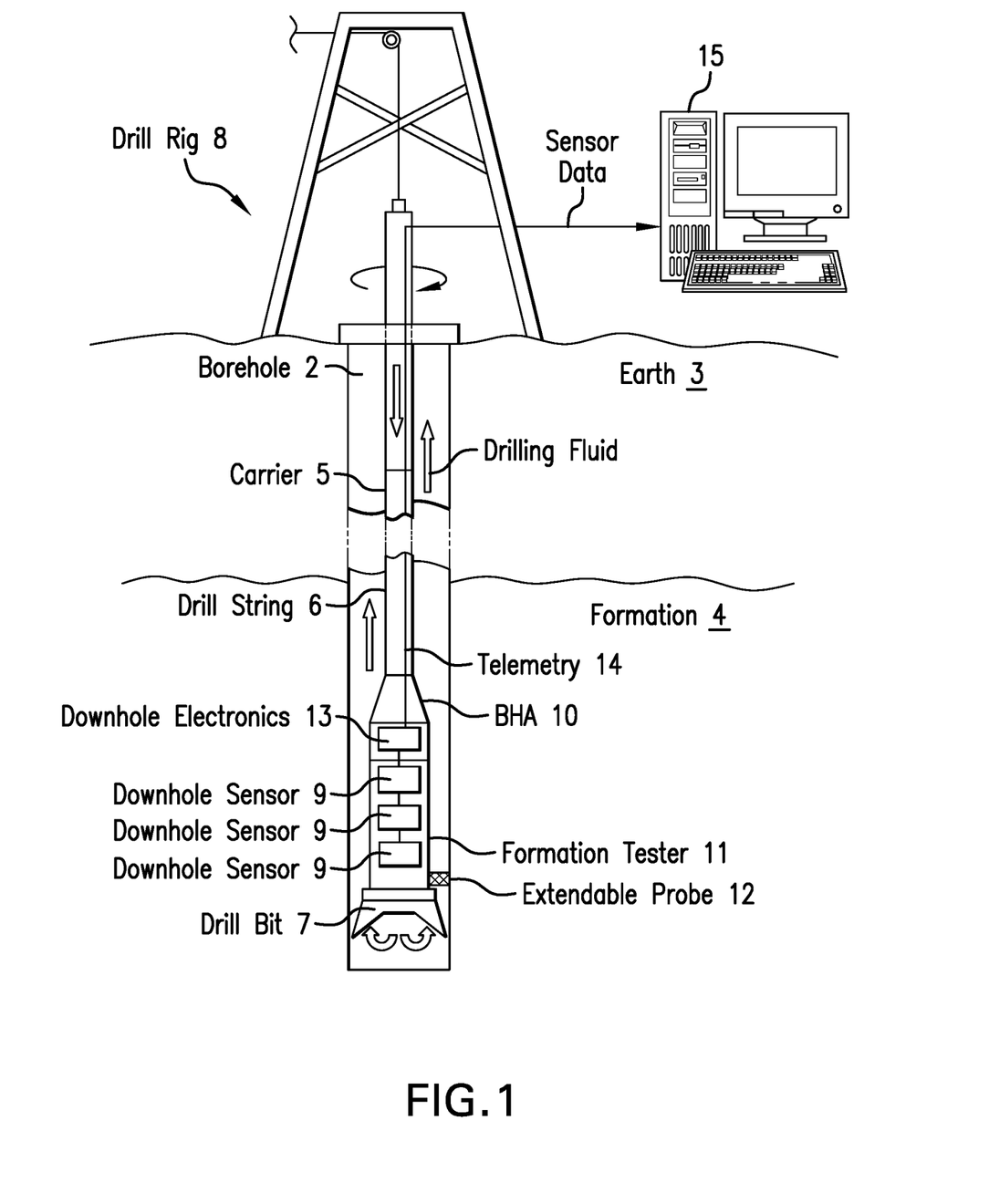
FIG. 1 is a cross-sectional view of an embodiment of a downhole sensor disposed in a borehole penetrating the earth.

FIG. 1 is a cross-sectional view of an embodiment of a bottomhole assembly (BHA) 10 disposed in a borehole 2 penetrating the earth 3 having a formation 4. A carrier 5 is configured to convey the BHA 10 through the borehole 2. In one or more embodiments, the carrier 5 is a drill string 6 in a logging-while-drilling (LWD) embodiment. Alternatively, the carrier 5 can be an armored wireline in an embodiment referred to as wireline logging. Coupled to the distal end of the drill string 6 is a drill bit 7 configured to cut or disintegrate rock to form the borehole 2. A drill rig 8 is configured to conduct drilling operations such as rotating the drill string 6 and thus the drill bit 7 in order to drill the borehole 2. In addition, the drill rig 8 may be configured to pump drilling fluid or mud through the drill string 6 in order to flush cuttings from the borehole 2 and lubricate the drill bit 7.

Disposed in the BHA 10 is a formation tester 11. The formation tester 11 is configured to extract a sample of formation fluid, such as hydrocarbons of interest, through a wall of the borehole 2 using an extendable probe 12. One or more sensors 9 are configured to sense multiple physical properties of the fluid sample downhole. Non-limiting embodiments of the physical properties include density, viscosity, sound speed, pressure, temperature, and compressibility. A single physical property may be sensed by one sensor 9 or multiple physical properties may be sensed by one sensor 9. Sensor data may be processed downhole by downhole electronics 13. Alternatively, sensor data may be transmitted to the surface of the earth using telemetry 14 and received for processing by a surface computer processing system 15. In addition, sensor data processing functions may be performed by a combination of the downhole electronics 13 and the surface computer processing system 15. Non-limiting embodiments of the telemetry include wired drill pipe and pulsed-mud telemetry. A depth at which the fluid sample is extracted may be recorded in order to correlate the sensed physical properties with the depth at which the corresponding sample was extracted. Accordingly, the chemical composition may be determined as a function of depth. It can be appreciated that sensor data can be processed as soon as it is received and thus provide answers to a user in real time.

Figure 2:
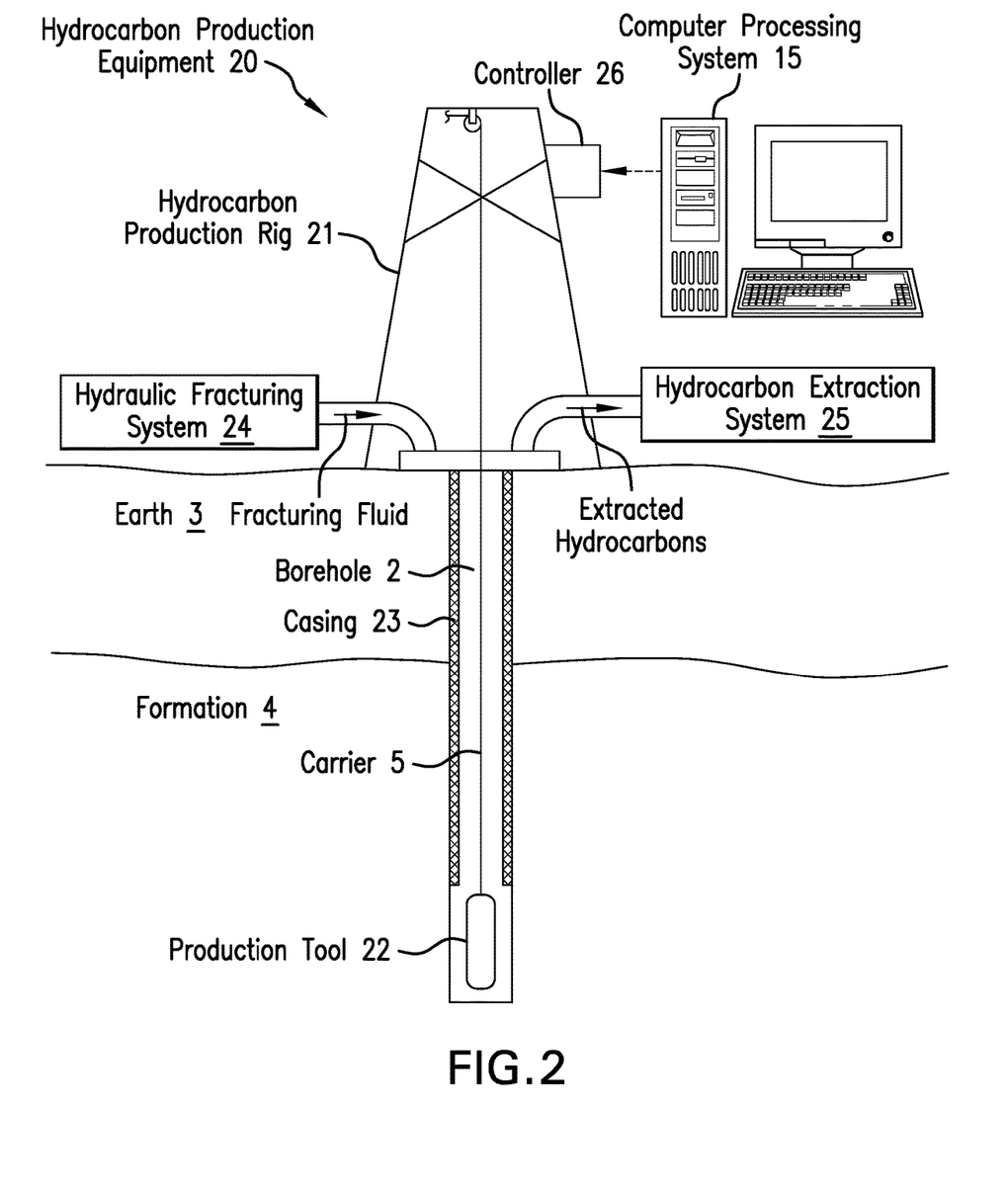
FIG. 2 is a cross-sectional view of an embodiment of hydrocarbon production equipment.

FIG. 2 is a cross-sectional view of an embodiment of hydrocarbon production equipment 20 that is configured to perform hydrocarbon production actions based upon knowing the chemical composition of the hydrocarbons of interest. As the chemical composition may be presented as a function of depth, this information may be used to determine a depth at which certain hydrocarbon production actions are performed. The hydrocarbon production equipment 20 may include a hydrocarbon production rig 21 configured to conduct hydrocarbon production actions such as lowering or raising a production tool 22 in the borehole 2. In one or more embodiments, the production tool 22 is configured to perforate a casing 23 lining the borehole 2 at a selected depth or range of depths. The hydrocarbon production equipment 20 may also include a hydraulic fracturing system 24 configured to hydraulically fracture the formation 4 in a selected depth interval. The hydrocarbon production equipment 20 may also include a hydrocarbon extraction system 25 configured to pump and process hydrocarbons from the formation 4. The chemical composition of the hydrocarbons of interest can give an indication as to the state the hydrocarbons of interest at the surface so that they can be processed appropriately. The hydrocarbon extraction system 25 may include pumps, valves and storage facilities (all not shown) appropriate for the chemical composition of the hydrocarbons of interest being extracted. For example, a hydrocarbon extraction system for a chemical composition indicating predominantly oil may be different from a hydrocarbon extraction system for a chemical composition indicating predominantly gas. Similarly, a hydrocarbon extraction system for light oil may be different from a hydrocarbon extraction system for heavy oil. A controller 26 may be used to control the hydrocarbon production functions and/or configurations and may receive input based on the estimated hydrocarbon chemical composition and optional corresponding depth from the surface processing system 15.

Figure 3:
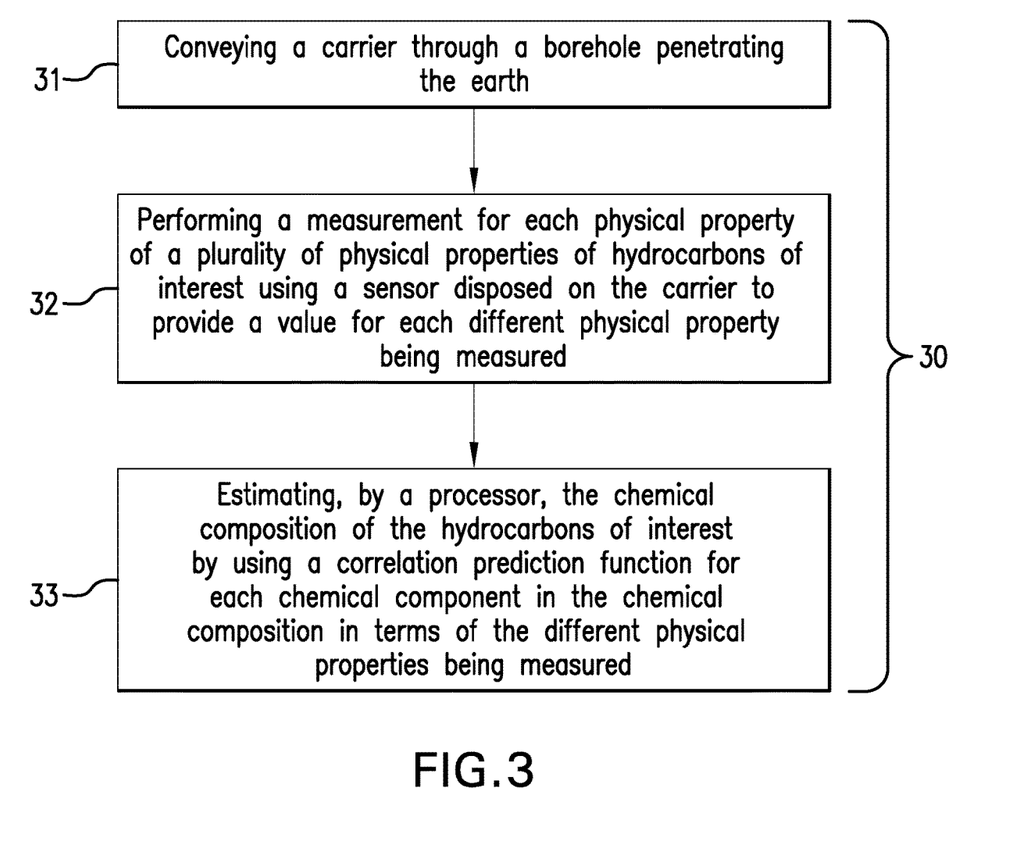
FIG. 3 is a flow chart for a method for estimating a chemical composition of hydrocarbons downhole.

FIG. 3 is a flow chart for a method 30 for estimating a chemical composition of hydrocarbons of interest. Block 31 calls for conveying a carrier through a borehole penetrating the earth. Non-limiting embodiments of the carrier include a wireline, a drill string, coiled tubing, and a slick line.

Block 32 calls for performing a measurement for each physical property of a plurality of physical properties of hydrocarbons of interest using a sensor disposed on the carrier to provide a value for each different physical property being measured. Non-limiting embodiments of the physical properties being sensed and measured include density, viscosity, sound speed, temperature, pressure, and compressibility. The sensor can represent a single sensor for each physical property sensed. Alternatively, a single sensor can sense two or more of the physical properties, such as the tuning fork sensor, which can measure both density and viscosity.

Block 33 calls for estimating, by a processor, the chemical composition of the hydrocarbons of interest by using a correlation prediction function for each chemical component in the chemical composition in terms of the different physical properties being measured. In one or more embodiments, the correlation prediction function is a mathematical equation for each chemical component in the chemical composition such that a concentration of the chemical component in the chemical composition can be predicted by entering the values of the measured physical properties. For example, the concentrations of methane (C1), ethane (C2), propane (C3), butane (C4), pentane (C5), hexane (C6), and heptane (C7) may be estimated by inputting the values of measured physical properties, a, b, c, d, e, and f into the following correlation prediction functions $f_1$, $f_2$, $f_3$, $f_4$, $f_5$, $f_6$, and $f_7$:

$C1=f_1(a,b,c,d,e,f)$
$C2=f_2(a,b,c,d,e,f)$
$C3=f_3(a,b,c,d,e,f)$
$C4=f_4(a,b,c,d,e,f)$
$C5=f_5(a,b,c,d,e,f)$
$C6=f_6(a,b,c,d,e,f)$
$C7=f_7(a,b,c,d,e,f)$

Figure 7A:
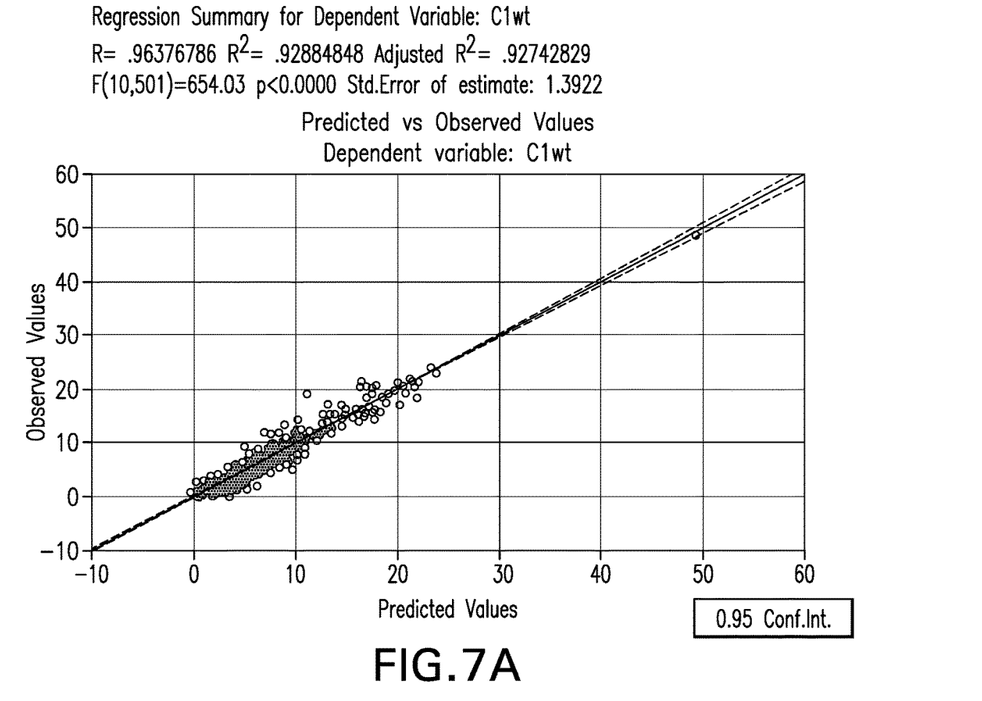
FIGS. 7A-7G, collectively referred to as FIG. 7, depict aspects of observed values versus predicted values for chemical components in a chemical composition of a hydrocarbon of interest.
Figure 7B:
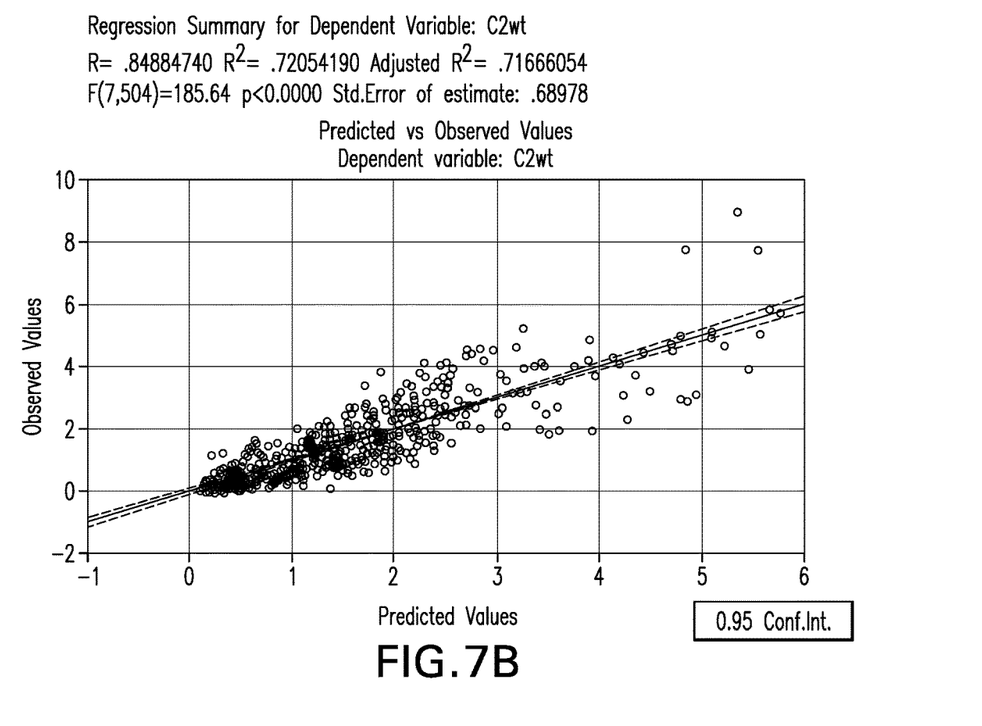
Figure 7C:
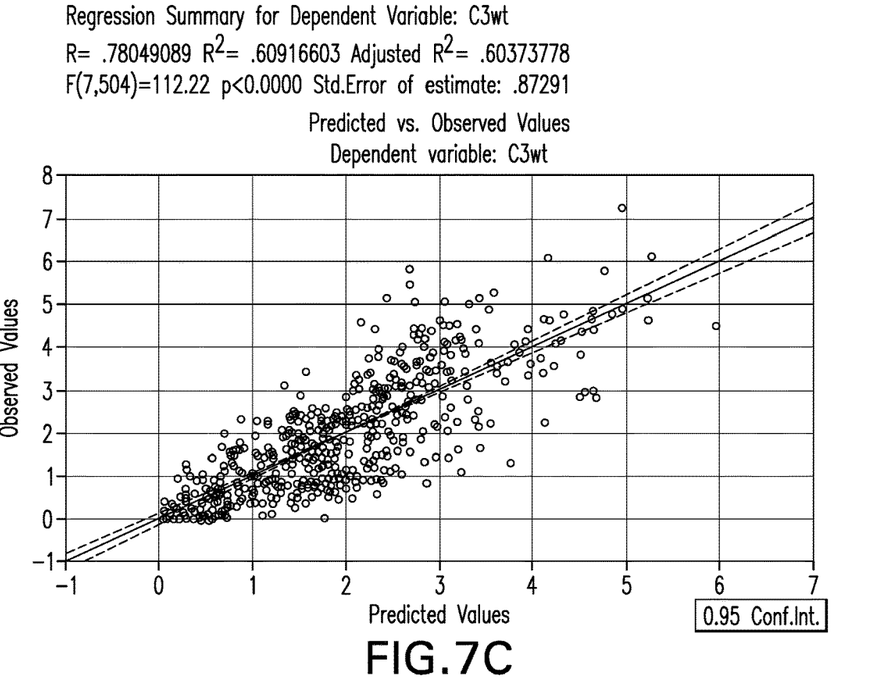
Figure 7D:
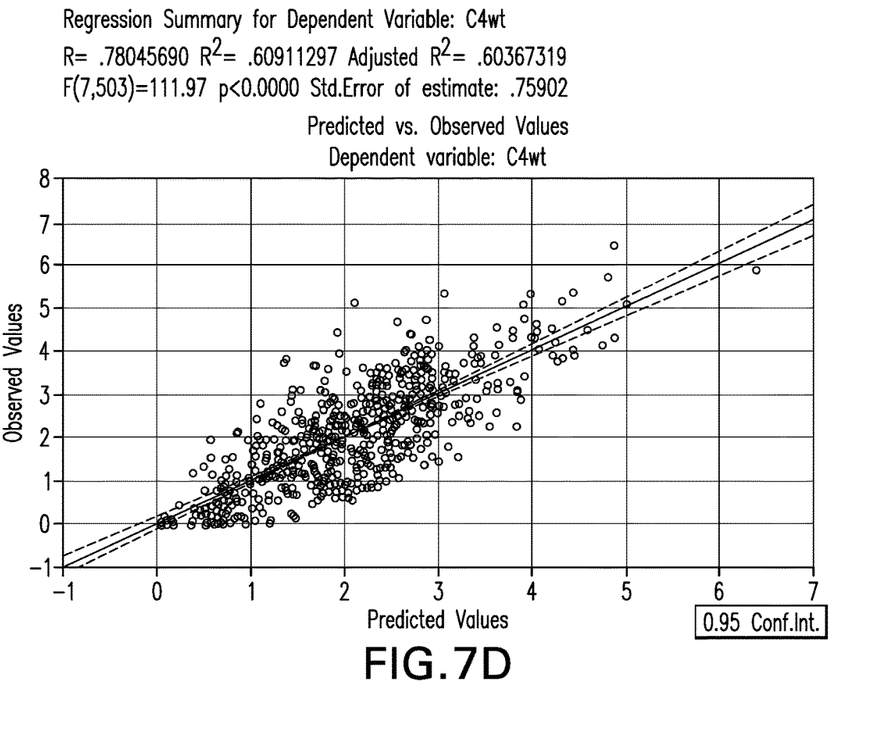
Figure 7E:
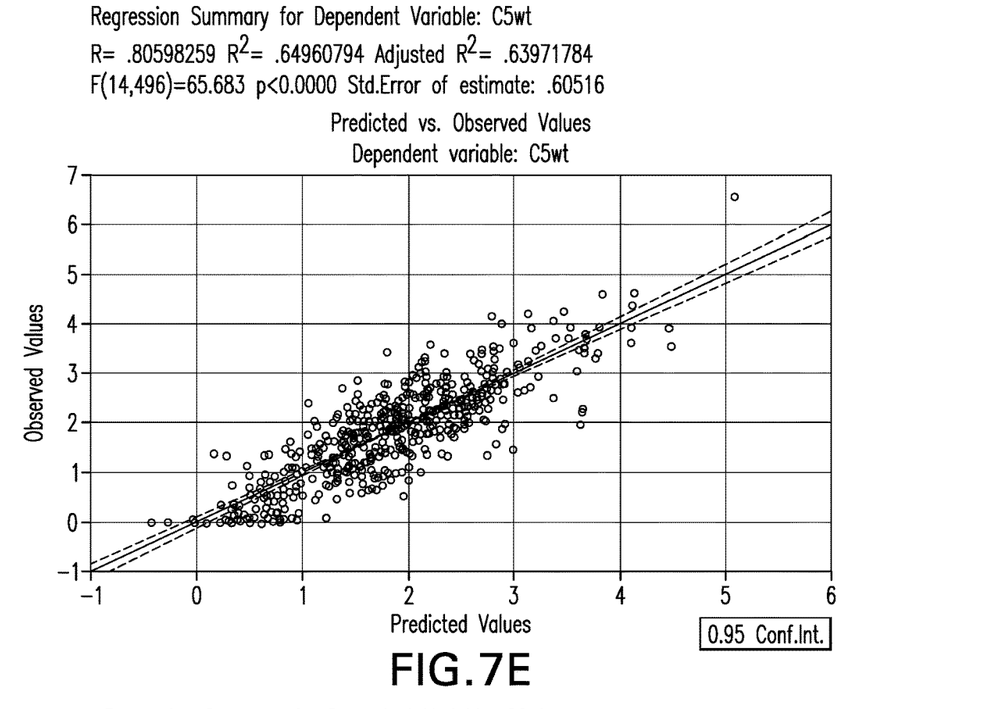
Figure 7F:
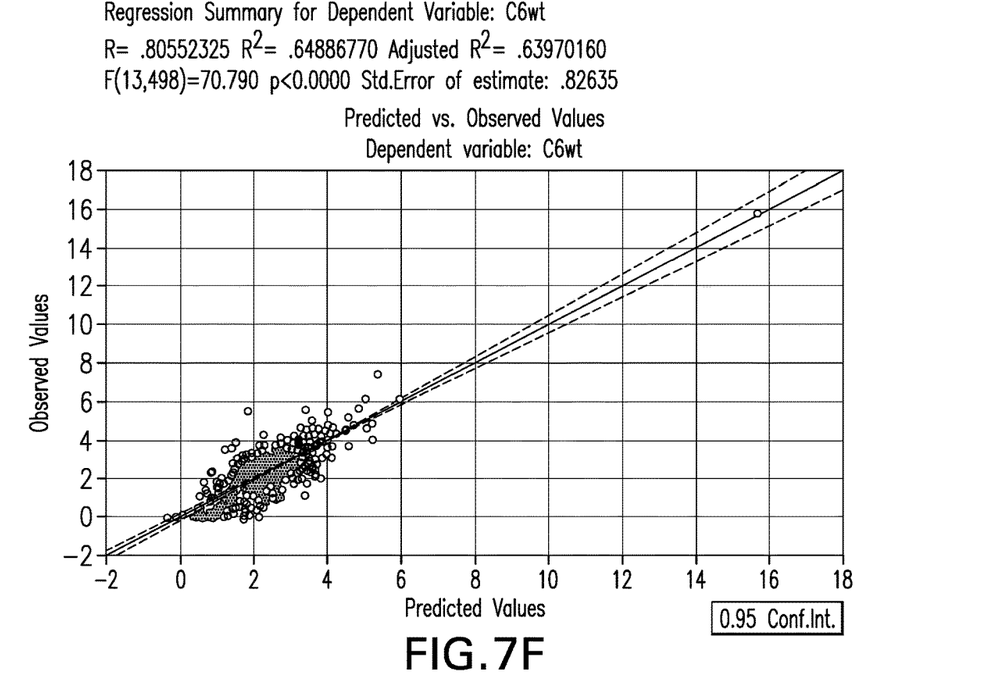
Figure 7G:
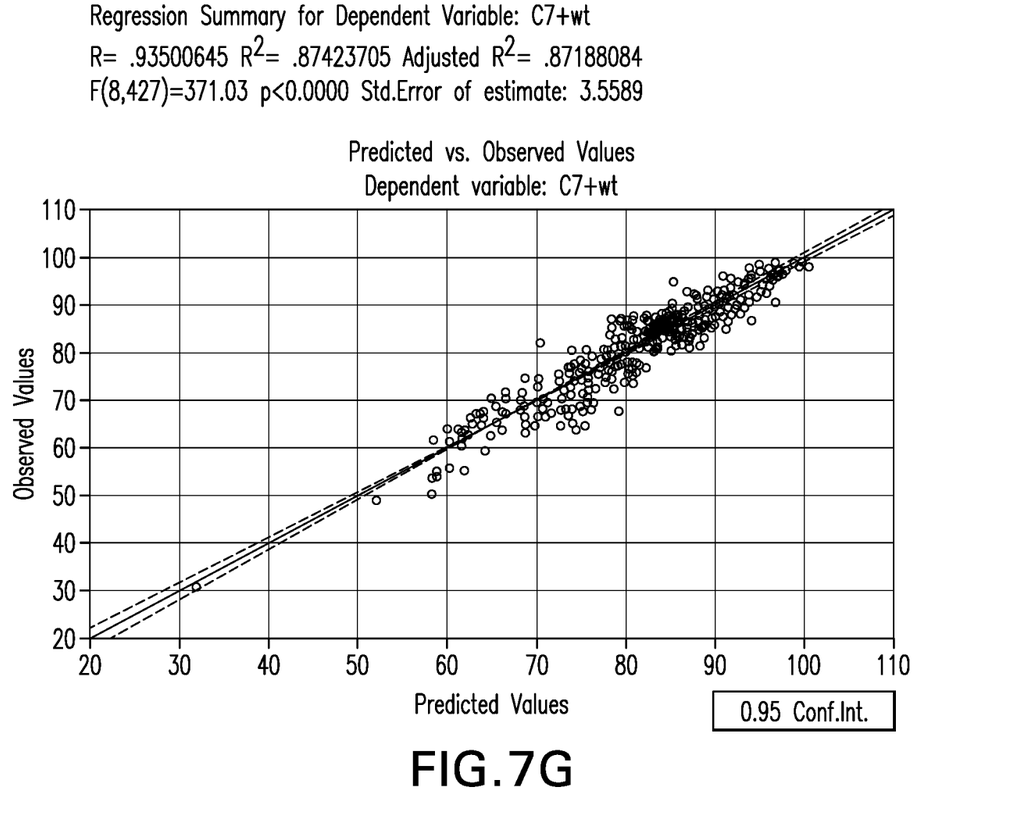

In one or more embodiments, carbon chains greater than C7 may be grouped together with C7 and simply referred to as C7+. For example, for the methane weight percentage, C1wt, the single most correlating composite independent variable for a set of approximately 500 live crude oils is the reciprocal of the product of temperature (° K) with density squared (g/cc) yielding the correlation prediction function, $C1wt=-9.80587598+2955.4188/(D^2T)$ but the fraction of data explained by this correlation ($R^2$) is only 0.728 and the standard error of calibration (SEC) is 2.700 in the prediction of weight percent. The next most correlating variable that the software used (Statistica) added during step forward regression was the pressure (kpsi) yielding the equation, $C1wt=-10.4650253+2544.13363/(D^2T)+0.700564866$ P, which has an $R^2=0.858$ with an SEC=1.954. Continuing on, subject to the requirement that all independent variables in the model have a statistical probability of less than 5% that its corresponding regression coefficient might actually be zero, an $R^2=0.929$ and SEC=1.392 are obtained as shown in FIG. 7A using ten composite independent variables. Similarly, FIGS. 7B-7G show regression results for predicted versus observed values for C2wt, C3wt, C4wt, C5wt, C6wt, and C7+wt percentages. These plots are not all at the same scale so, for enlarged-scale plots that cover a smaller range, the correlations do not visually appear as good as for plots covering a much larger range even when the SEC is actually lower (better). Not shown are some good regressions for isobutane and normal butane where iC4wt+nC4wt=C4wt (i=iso and n=normal) and for isopentane and normal pentane where iC5wt+nC5wt=C5wt. Although the above discussion describes step-forward multiple linear regression, other linear regression methods can be used such as Principal Components Regression (PCR) or Partial Least Square regression (PLS). Other modeling methods, such as Neural Networks (NN), which can create linear or nonlinear models, could also be used. Note that, if there is random error, $s_L$, in the laboratory values for C1, C2, C3, ... C7+ in the training set, then the model's Standard Error of Calibration will include both that lab imprecision, $s_L$, as well as any modeling error, $s_M$, so that the apparent $SEC^2 = Sqrt(s_L^2 + s_M^2)$. Linear least squares models fit a hyperplane to a set of data points in hyperspace so that the sum of the squares of the distances of points above the hyperplane to it will equal the sum of the squares of the distances of points below the hyperplane to it. Therefore, the hyperplane model acts to average out random lab error in the training set calibration values, which means that the model's actual prediction performance on unknown samples can be better than the SEC (See R. DiFoggio, *Examination of Some Misconceptions about Near-Infrared Analysis*, Applied Spectroscopy January 1995 49: 67-75, doi:10.1366/0003702953963247). Block 33 may also include inputting the measured values of the different physical properties into the correlation prediction function and obtaining as output the chemical composition of the hydrocarbon sample being evaluated. The output may then be transmitted as a signal to a user for performing further actions related to knowing the chemical composition.

Figure 4:
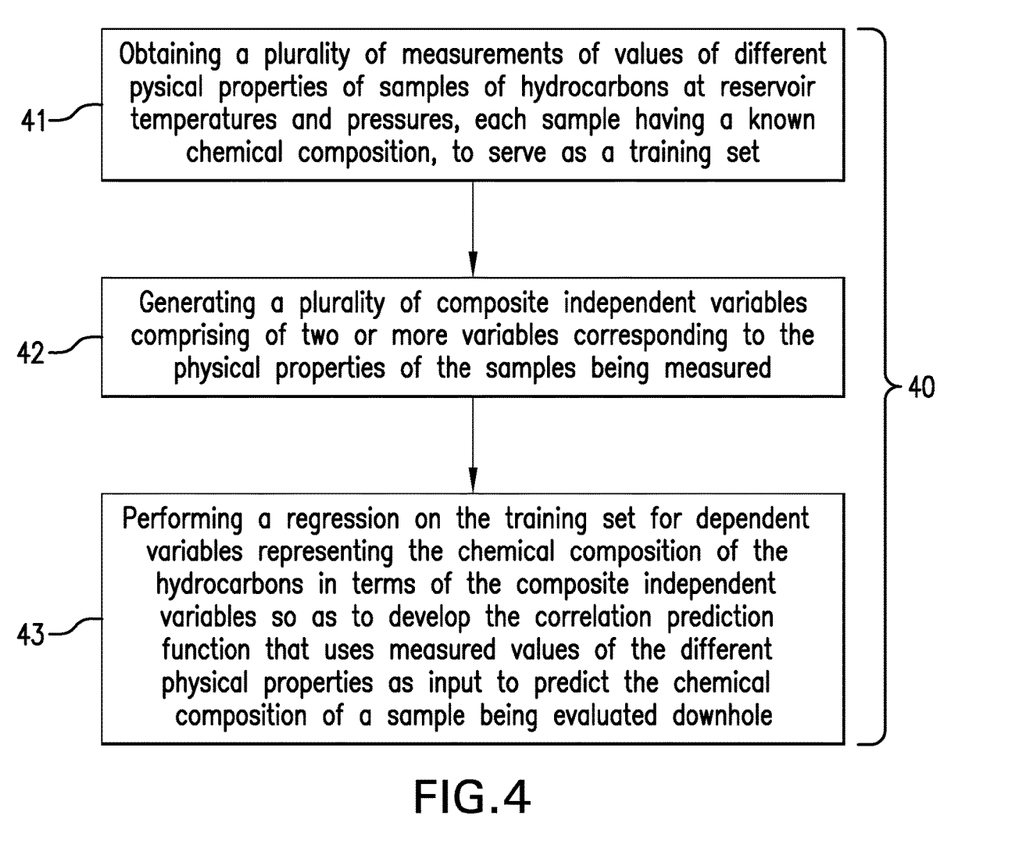
FIG. 4 is a flow chart for a method for generating a correlation that correlates a chemical composition of hydrocarbons to a plurality of measured physical parameters.
Figure 6:
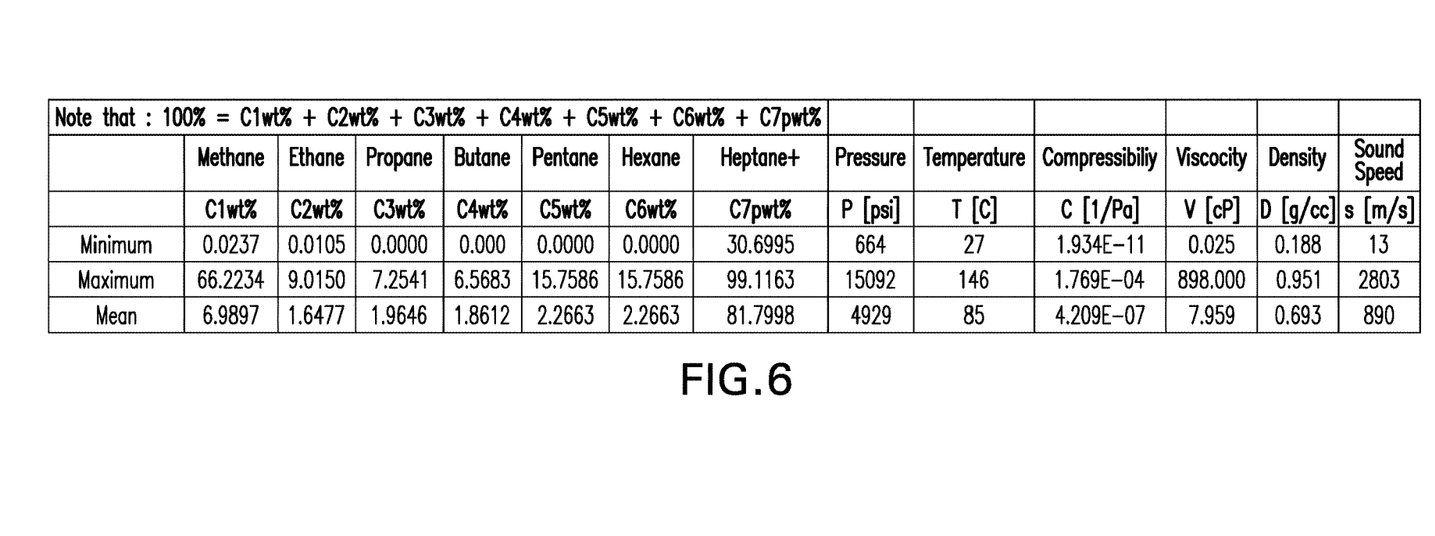
FIG. 6 presents one example of ranges of measured physical properties of samples having ranges of known chemical compositions.

FIG. 4 is a flow chart for a method 40 for generating a correlation prediction function that correlates measured physical properties to a chemical composition. Block 41 calls for obtaining a plurality of measurements of values of different physical properties of samples of hydrocarbons at reservoir temperatures and pressures, each sample having a known chemical composition, to serve as a training set. To be clear, the training set has measured values of physical properties of multiple samples of different hydrocarbons at in-situ temperatures and pressures, each sample having a measured chemical composition. The different physical properties are those physical properties used in the correlation prediction function discussed above. This block may also include performing the plurality of measurements using a sensor. FIG. 6 presents one example of ranges of measured physical properties of samples having ranges of known chemical compositions.

Block 42 calls for generating a plurality of composite independent variables comprising two or more variables corresponding to the physical properties of the samples being measured. That is, each composite independent variable includes two or more variables with each variable representing a different physical property. For example, composite independent variable 1 (CIV1) may represent $(a^x \cdot b^y)$ for physical property variables a and b. Composite independent variable 2 (CIV2) may represent $(a^x/b^y)$. With more physical property values and many choices for exponents, there can be many types of combinations and permutations resulting in a large number of composite independent variables such as in the hundreds or even more.

Figure 5A:
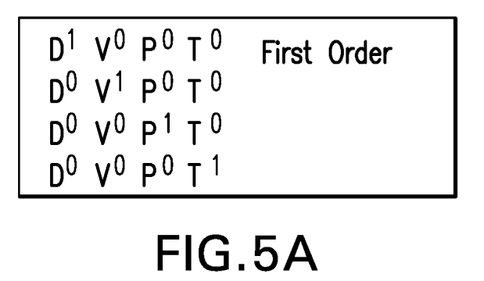
FIGS. 5A-5C, collectively referred to as FIG. 5, depict aspects of generating composite independent variables for regression.
Figure 5B:
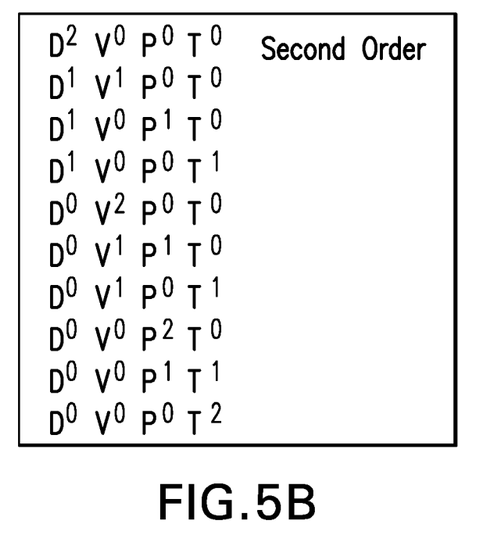
Figure 5C:
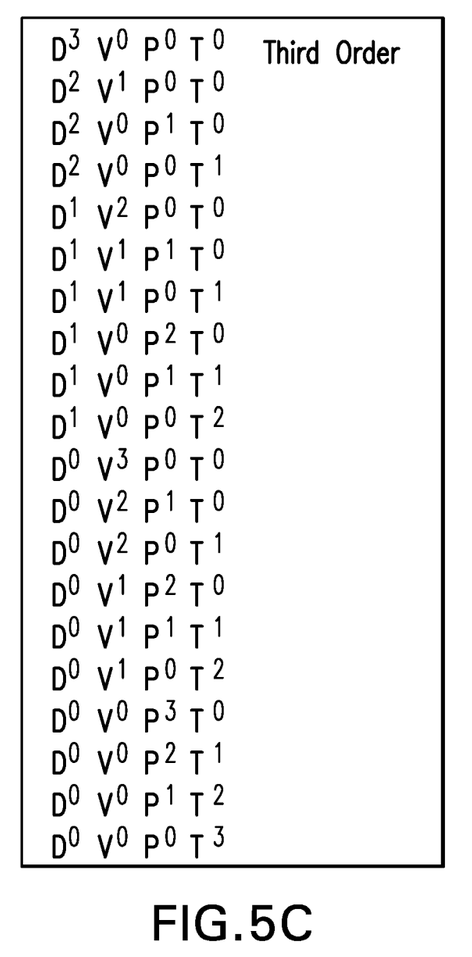

FIG. 5 illustrates one example of how to generate an expanded set of linearly-independent composite independent variables from an original set of four independent variables, Density (D), Viscosity (V), Pressure (P), and Temperature (T). Of course, an even larger original set of independent variables could be used, which also included Compressibility (C) and Sound Speed (SS), but that would have made this example more complex for teaching purposes. This example of a process is similar to individual product terms of a multinomial expansion in which the sum of the exponents of each term is equal to the power to which the multinomial is taken. For the example below, shown as "Third Order" in FIG. 5C, the multinomial power is 3 and the sum of the exponents in each term is also 3.

$(D+V+P+T)^3 = 1 \, D^3 \, V^0 \, P^0 \, T^0 + 3 \, D^2 \, V^1 \, P^0 \, T^0 + 3 \, D^2 \, V^0 \, P^1 \, T^0 + 3 \, D^2 \, V^0 \, P^0 \, T^1 + 3 \, D^1 \, V^2 \, P^0 \, T^0 + 6 \, D^1 \, V^1 \, P^1 \, T^0 + 6 \, D^1 \, V^1 \, P^0 \, T^1 + 3 \, D^1 \, V^0 \, P^2 \, T^0 + 6 \, D^1 \, V^0 \, P^1 \, T^1 + 3 \, D^1 \, V^0 \, P^0 \, T^2 + 1 \, D^0 \, V^3 \, P^0 \, T^0 + 3 \, D^0 \, V^2 \, P^1 \, T^0 + 3 \, D^0 \, V^2 \, P^0 \, T^1 + 3 \, D^0 \, V^1 \, P^2 \, T^0 + 6 \, D^0 \, V^1 \, P^1 \, T^1 + 3 \, D^0 \, V^1 \, P^0 \, T^2 + 1 D^0 \, V^0 \, P^3 \, T^0 + 3 \, D^0 \, V^0 \, P^2 \, T^1 + 3 \, D^0 \, V^0 \, P^1 \, T^2 + 1 D^0 \, V^0 \, P^0 \, T^3$

In FIG. 5A ("First Order") the multinomial power is one, while in FIG. 5B ("Second Order") the multinomial power is two. To further expand the list of linearly-independent composite variables, D could be replaced by its reciprocal 1/D in each term. Alternatively, V could be replaced by its reciprocal or P by its reciprocal or T by its reciprocal. Next, any two of the original variables, D, V, P, and T could be replaced by their reciprocals. Next, any combination of three variables or all four variables could be replaced by their reciprocals. Similarly, fractional power replacements for variables such as square roots could also be used. Logarithms may also be used. A simple way to exhaustively prepare a list of all n-order terms of an m-term multinomial taken to the n-th power is to count in the number base, $(n+1)$, from 1 to $(n+1)^m - 1$ and then to retain only those sets of digits for which digit sum is n, which can easily be done in a spreadsheet. Note that the composite independent variables created in this way will also be linearly independent of one another, which is important when performing multiple linear regression so that there will be no linear redundancy in the set of independent variables.

Referring back to FIG. 4, Block 43 calls for performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole. Downhole evaluation relates to obtaining a hydrocarbon sample downhole and performing measurements downhole of different physical properties under in-situ conditions of temperature and pressure to obtain values of the different physical properties. "Regression" relates to estimating a mathematical relationship (i.e., correlation function) between the chemical composition of the hydrocarbons of interest and the composite independent variables using the training set. Different types of regression analysis techniques may be used. In one or more embodiments, a step forward Multiple Linear Regression (MLR) with substitution is used. In this technique, the choice or predictive composite variables is carried out by an automatic procedure such as an algorithm first proposed by Efroymson in 1960. This procedure generally takes the form of a sequence of F-tests or t-tests, but other techniques are possible, such as adjusted $R^2$ in order to select the composite variables providing the best fit. The step forward multiple linear regression involves starting with no variables in the model, testing the addition of each variable using a chosen model fit criterion, adding the variable (if any) whose inclusion gives the most statistically significant improvement of the fit, and repeating this process until none improves the model to a statistically significant extent. Another type of regression analysis is backward elimination, which involves starting with all candidate variables, testing the deletion of each variable using a chosen model fit criterion, deleting the variable (if any) whose loss gives the most statistically insignificant deterioration of the model fit, and repeating this process until no further variables can be deleted without a statistically significant loss of fit. Yet another, type of regression analysis is bidirectional elimination, a combination of the above, testing at each step for variables to be included or excluded. Commercial software, such as Statistica (sold by StatSoft of Tulsa, Okla.) is readily available to perform such regression analysis techniques.

Note that "with substitution" can be significant because, in step forward multiple linear regression, the algorithm starts out with the highest correlating independent variable and then seeks a second independent variable that provides the most complementary information to the first. However, upon picking a third independent variable, that third variable, together with the second, may model the data so well that the first variable becomes statistically insignificant, in which case the first variable is dropped. Specifically, the user sets two F-test thresholds, one for entering a new independent variable into the model and another for removing a current independent variable from the model. This situation can occur when the second and third independent variables are not individually highly correlated to the dependent variable but they provide highly complementary information so that, together, they provide better correlation than the first variable alone so that inclusion of the first variable in a three-variable model becomes statistically insignificant and the first variable is then dropped from the model.

The methods and apparatuses disclosed herein provide several advantages. One advantage is that the physical properties required for being input into the correlation function are readily measurable downhole and avoid the expense and time necessary to transfer a sample from the formation to a surface laboratory under in-situ conditions. Another advantage is that because the physical properties can be readily measured downhole, the methods disclosed herein can be implemented in real time instead of waiting months for a surface laboratory analysis. By receiving hydrocarbon chemical composition information in real time, petroleum analysts and engineers can quickly implement or alter completion procedures and/or configure hydrocarbon production equipment based on the chemical composition. Real time analysis of crude oil composition allows the operator to make much earlier ordering decisions for the specific types of expensive and long lead time production and processing equipment that will be needed.

Yet another advantage is that reservoir connectivity can be determined based on the chemical composition of layers being the same or different. Reservoir connectivity determination can be useful in planning and executing plans for borehole or reservoir completion. Disconnected reservoirs will need separate wells to drain them, which can be a very expensive undertaking, especially offshore.

Set forth below are some embodiments of the foregoing disclosure:

Embodiment 1: A method for estimating a chemical composition of hydrocarbons of interest, the method comprising: performing a measurement for each physical property of a plurality of physical properties of the hydrocarbons of interest using a sensor to provide a value for each different physical property being measured; and estimating, by a processor, the chemical composition of the hydrocarbons of interest by using a correlation prediction function for each chemical component in the chemical composition in terms of the different physical properties being measured.

Embodiment 2: The method according to any prior embodiment, further comprising generating the prediction function by: obtaining a plurality of measurements of values of different physical properties of samples of hydrocarbons at reservoir temperatures and pressures, each sample having a known chemical composition, to serve as a training set; generating a plurality of composite independent variables comprising two or more variables corresponding to the physical properties of the samples being measured; and performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole.

Embodiment 3: The method according to any prior embodiment, wherein the chemical composition comprises a relative concentration for each of two or more carbon molecules.

Embodiment 4: The method according to any prior embodiment, wherein the two or more carbon molecules comprises methane (C1), ethane (C2), propane (C3), butane (C4), pentane (C5), hexane (C6), and heptane and higher (C7+).

Embodiment 5: The method according to any prior embodiment, wherein the prediction function comprises a prediction function for each of the two or more carbon molecules.

Embodiment 6: The method according to any prior embodiment, wherein the composite independent variables comprise terms of a multinomial expansion of variables representing the plurality of physical properties being measured.

Embodiment 7: The method according to any prior embodiment, wherein at least one variable in the multinomial expansion is a reciprocal of a physical property being measured.

Embodiment 8: The method according to any prior embodiment, wherein the regression comprises a step forward multiple linear regression with substitution.

Embodiment 9: The method according to any prior embodiment, wherein the plurality of physical properties comprises at least two selections from a group consisting of density, viscosity, sound speed, pressure, and temperature.

Embodiment 10: The method according to any prior embodiment, wherein the estimating is performed in real time upon receiving the measurements for each physical property in the plurality of physical properties of the hydrocarbons of interest.

Embodiment 11: The method according to any prior embodiment, further comprising performing a hydrocarbon production action using the estimated chemical composition of the hydrocarbons of interest.

Embodiment 12: The method according to any prior embodiment, wherein the hydrocarbon production action comprises hydraulic fracturing an earth formation containing the hydrocarbons in a selected range of depths.

Embodiment 13: The method according to any prior embodiment, further comprising conveying a carrier through a borehole penetrating the earth, wherein the sensor is disposed on the carrier and the measurement for each physical property is performed downhole.

Embodiment 14: An apparatus for estimating a chemical composition of hydrocarbons of interest, the apparatus comprising: a sensor configured to perform a measurement for each physical property in a plurality of physical properties of the hydrocarbons of interest to provide a value for each different physical property being measured; and a processor configured to estimate the chemical composition of the hydrocarbons of interest by using a correlation prediction function for each chemical component in the chemical composition in terms of the different physical properties being measured.

Embodiment 15: The apparatus according to any prior embodiment, further comprising a carrier configured to be conveyed through a borehole penetrating the earth, wherein the sensor is disposed on the carrier and is configured to perform the measurement for each physical property downhole.

Embodiment 16: The apparatus according to any prior embodiment, wherein the carrier comprises a wireline, a drill string, coiled tubing, or a slickline.

Embodiment 17: The apparatus according to any prior embodiment, wherein the sensor comprises at least two selections from a group consisting or a density sensor, a viscosity sensor, a sound speed sensor, a pressure sensor, and a temperature sensor.

Embodiment 18: The apparatus according to any prior embodiment, further comprising a user interface configured to receive a signal from the processor, the signal comprising the chemical composition of the hydrocarbons of interest.

Embodiment 19: The apparatus according to any prior embodiment, wherein the processor is further configured to generate the prediction function by: obtaining a plurality of measurements of values of different physical properties of samples of hydrocarbons at reservoir temperatures and pressures, each sample having a known chemical composition, to serve as a training set; generating a plurality of composite independent variables comprising two or more variables corresponding to the physical properties of the samples being measured; and performing a regression on the training set for dependent variables representing the chemical composition of the hydrocarbons in terms of the composite independent variables so as to develop the correlation prediction function that uses measured values of the different physical properties as input to predict the chemical composition of a sample being evaluated downhole.

In support of the teachings herein, various analysis components may be used, including a digital and/or an analog system. For example, the sensors 9, the formation tester 11, the downhole electronics 13, and/or the surface computer processing system 15 may include digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Non-limiting embodiments of carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured. The terms "first" and "second" are used to distinguish elements and are not used to denote a particular order.

The flow diagrams depicted herein are just an example. There may be many variations to these diagrams or the steps (or operations) described therein without departing from the spirit of the invention. For instance, the steps may be performed in a differing order, or steps may be added, deleted or modified. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a concentration of a chemical component of a crude oil of interest, the method comprising:
performing a measurement for each physical property of a plurality of physical properties of the crude oil of interest using a sensor to provide a value for each different physical property being measured;

generating, by a processor, a correlation prediction function for the chemical component in terms of the different physical properties being measured, the correlation prediction function comprising multiple composite linearly independent variables derived from the different physical properties; and estimating, by the processor, the concentration of the chemical component of the crude oil of interest by using the correlation prediction function with the measured value of the different physical properties being measured being input into the correlation prediction function;

wherein the chemical component comprises at least one of methane (C1), ethane (C2), propane (C3), butane (C4), pentane (C5), hexane (C6), and a combination of heptane and any higher carbon number (C7+).

2. The method according to claim 1, wherein generating the correlation prediction function comprises:

obtaining a plurality of measurements of values of different physical properties of samples of different hydrocarbons at reservoir temperatures and pressures, each sample having a known concentration of the chemical component, to serve as a training set;

generating a plurality of composite linearly independent variables comprising two or more variables corresponding to the physical properties of the samples being measured; and performing a regression on the training set for dependent variables representing the concentration of the chemical component of the hydrocarbons at the reservoir temperatures and pressures in terms of the composite linearly independent variables so as to develop the correlation prediction function that uses measured values of the different physical properties as input to predict the concentration of the chemical component of a sample of the crude oil of interest being evaluated downhole.

3. The method according to claim 2, wherein the chemical composition comprises a relative concentration for each of two or more carbon molecules.

4. The method according to claim 3, wherein the correlation prediction function comprises a prediction of concentration for each of the methane (C1), ethane (C2), propane (C3), butane (C4), pentane (C5), hexane (C6), and the combination of heptane and any higher carbon number (C7+).

5. The method according to claim 2, wherein the regression comprises a step forward multiple linear regression with substitution.

6. The method according to claim 1, wherein the composite linearly independent variables comprise terms of a multinomial expansion of variables representing the plurality of physical properties being measured.

7. The method according to claim 6, wherein at least one variable in the multinomial expansion is a reciprocal of a physical property being measured.

8. The method according to claim 1, wherein the plurality of physical properties comprises at least two selections from a group consisting of density, viscosity, sound speed, pressure, and temperature.

9. The method according to claim 1, wherein the estimating is performed in real time upon receiving the measurements for each physical property in the plurality of physical properties of the crude oil of interest.

10. The method according to claim 1, further comprising performing a hydrocarbon production action using the estimated concentration of the chemical component of the crude oil of interest.

11. The method according to claim 10, wherein the hydrocarbon production action comprises hydraulic fracturing an earth formation containing the hydrocarbons in a selected range of depths.

12. The method according to claim 1, further comprising conveying a carrier through a borehole penetrating the earth, wherein the sensor is disposed on the carrier and the measurement for each physical property is performed downhole.

13. An apparatus for estimating a concentration of a chemical component of crude oil of interest, the apparatus comprising:

a sensor configured to perform a measurement for each physical property in a plurality of physical properties of the crude oil of interest to provide a value for each different physical property being measured; and a processor configured to: generate a correlation prediction function for the chemical component in terms of the different physical properties being measured, the correlation prediction function comprising multiple composite linearly independent variables derived from the different physical properties; and estimate the concentration of the chemical component of the crude oil of interest by using the correlation prediction function with the measured value of the different physical properties being measured being input into the correlation prediction function;

wherein the chemical component comprises at least one of methane (C1), ethane (C2), propane (C3), butane (C4), pentane (C5), hexane (C6), and a combination of heptane and any higher carbon number (C7+).

14. The apparatus according to claim 13, further comprising a carrier configured to be conveyed through a borehole penetrating the earth, wherein the sensor is disposed on the carrier and is configured to perform the measurement for each physical property downhole.

15. The apparatus according to claim 14, wherein the carrier comprises a wireline, a drill string, coiled tubing, or a slickline.

16. The apparatus according to claim 13, wherein the sensor comprises at least two selections from a group consisting or a density sensor, a viscosity sensor, a sound speed sensor, a pressure sensor, and a temperature sensor.

17. The apparatus according to claim 13, further comprising a user interface configured to receive a signal from the processor, the signal comprising the concentration of the chemical component of the crude oil of interest.

18. The apparatus according to claim according to claim 13, wherein the processor is further configured to perform the following actions to generate the prediction function:

obtaining a plurality of measurements of values of different physical properties of samples of different hydrocarbons at reservoir temperatures and pressures, each sample having a known concentration of the chemical component, to serve as a training set;

generating a plurality of composite linearly independent variables comprising two or more variables corresponding to the physical properties of the samples being measured; and performing a regression on the training set for dependent variables representing the concentration of the chemical component of the at the reservoir temperatures and pressures in terms of the composite linearly independent variables so as to develop the correlation prediction function that uses measured values of the different physical properties as input to predict the concentration of the chemical component of a sample of the crude oil of interest being evaluated downhole.

\* \* \* \* \*